US011326192B2

(12) United States Patent
Rodighiero et al.

(10) Patent No.: US 11,326,192 B2
(45) Date of Patent: May 10, 2022

(54) VARIANT OF OLEAGINOUS YEAST AND ITS USE FOR THE PRODUCTION OF LIPIDS

(71) Applicant: Versalis S.p.A., San Donato Milanese (IT)

(72) Inventors: Valentina Rodighiero, Milan (IT); Giuliana Franzosi, Voghera (IT); Concetta Compagno, Spino D'Adda (IT); Claudia Capusoni, Milan (IT)

(73) Assignee: Versalis S.p.A., San Donato Milanese (IT)

( * ) Notice: Subject to any disclaimer, the term of this patent is extended or adjusted under 35 U.S.C. 154(b) by 82 days.

(21) Appl. No.: 16/631,188

(22) PCT Filed: Jul. 17, 2018

(86) PCT No.: PCT/IB2018/055301
§ 371 (c)(1),
(2) Date: Jan. 15, 2020

(87) PCT Pub. No.: WO2019/016703
PCT Pub. Date: Jan. 24, 2019

(65) Prior Publication Data
US 2020/0149076 A1 May 14, 2020

(30) Foreign Application Priority Data
Jul. 18, 2017 (IT) .................. 102017000081383

(51) Int. Cl.
*C12R 1/645* (2006.01)
*C12N 1/14* (2006.01)
*C12P 7/64* (2022.01)

(52) U.S. Cl.
CPC ............. *C12P 7/64* (2013.01); *C12N 1/145* (2021.05); *C12R 2001/645* (2021.05)

(58) Field of Classification Search
CPC ..... C12P 7/64; C12N 1/145; C12R 2001/645; Y02E 50/10
See application file for complete search history.

(56) References Cited

U.S. PATENT DOCUMENTS

2018/0223248 A1    8/2018   Bortolo et al.

FOREIGN PATENT DOCUMENTS

| WO | WO 2017/021931 A1 | 2/2017 | |
| WO | WO-2017021931 A1 * | 2/2017 | ............... C12N 1/02 |

OTHER PUBLICATIONS

Capusoni, C. et al., "Characterization of lipid accumulation and lipidome analysis in the oleaginous yeasts *Rhodosporidium azoricum* and *Trichosporon oleaginosus*," Bioresource Technology, vol. 238, Apr. 1, 2017, XP 085037180, pp. 281-289.

(Continued)

*Primary Examiner* — Olivia M. Wise
*Assistant Examiner* — Anjali Ajit Hirani
(74) *Attorney, Agent, or Firm* — Oblon, McClelland, Maier & Neustadt, L.L.P.

(57) ABSTRACT

The present invention relates to a variant of oleaginous yeast of the species *Trichosporon oleaginosus* characterized by mutations affecting cell wall synthesis that change the morphology thereof with respect to the wild-type strain of the same species. In particular, thanks to said mutations, cell aggregates are formed which, with respect to the wild-type strain of the same species, lower the viscosity of the culture broth, are more easily separable therefrom and thus make their recovery easier. Said variant of oleaginous yeast of the species *Trichosporon oleaginosus* is also characterized by yields of oleaginous cellular biomass and intracellular accumulation of lipids that are similar or even higher than those of the wild-type strain. Further, the present invention relates to a process for the production of lipids through said variant (Continued)

(A)                                   (B)

of oleaginous yeast of the species *Trichosporon oleaginosus*. The lipids thus obtained can be advantageously used as synthesis intermediates, particularly in the so-called "green chemistry" sector, or in the production of biofuels such as, for example, "biodiesel" or "green diesel", which can be used as such, or mixed with other fuels for transportation.

8 Claims, 3 Drawing Sheets

(56) References Cited

OTHER PUBLICATIONS

Meo, A. et al., "Lipid production with *Trichosporon oleaginosus* in a membrane bioreactor using microalgae hydrolysate," Journal of Biotechnology, vol. 241, Oct. 27, 2016, XP 029860697, pp. 1-10.
International Search Report dated Oct. 1, 2018 in PCT/IB2018/055301 filed on Jul. 17, 2018.

* cited by examiner (A) (B)

VARIANT OF OLEAGINOUS YEAST AND ITS USE FOR THE PRODUCTION OF LIPIDS

The present invention relates to a variant of oleaginous yeast of the species *Trichosporon oleaginosus*.

More in particular, the present invention relates to a variant of oleaginous yeast of the species *Trichosporon oleaginosus*, characterized by mutations affecting cell wall synthesis that change the morphology thereof with respect to the wild-type strain of the same species. In particular, thanks to said mutations, cell aggregates are formed which, with respect to the wild-type strain of the same species, lower the viscosity of the culture broth, are more easily separable therefrom and thus make their recovery easier.

Said variant of oleaginous yeast of the species *Trichosporon oleaginosus* is also characterized by yields of oleaginous cellular biomass and intracellular accumulation of lipids that are similar or even higher than those of the wild-type strain.

Further, the present invention relates to a process for the production of lipids through the cultivation of said variant of oleaginous yeast of the species *Trichosporon oleaginosus*.

The lipids thus obtained can be advantageously used as synthesis intermediates, particularly in the so-called "green chemistry" sector, or in the production of biofuels such as "biodiesel" or "green diesel", which can be used as such, or mixed with other fuels for transportation.

The production of lipids through microbiological methods is proposed as an advantageous alternative to current production methods from renewable sources. With respect to the extraction of lipids from plants, microbiological processes are more cost effective as they are more easily scalable, require less labour, and exploit the property of the microorganisms to quickly reproduce at the expense of low cost substrates, such as, for example, derivatives from the hydrolysis of lignocellulosic materials. Furthermore, they are independent from climatic factors and do not compete with the agricultural exploitation of soil for food purposes.

Particularly promising for this purpose are oleaginous yeasts, i.e. yeasts that can, under specific cultivation conditions, accumulate lipids, especially triglycerides, for over 25% of their dry weight. The use of oleaginous yeasts for the production of lipids is part of the prior art as described, for example, in: Meng X. et al, "*Renewable Energy*" (2009), Vol. 34, pag. 1-5; Galafassi S. et al, "*Bioresource Technology*" (2012), Vol. 111, pag. 398-403.

Generally, said lipids are obtained through the cultivation of oleaginous yeasts under aerobic conditions in bioreactors. Oleaginous yeasts are grown using sugar solutions that can be obtained from starchy plants or sugary fruits and are defined as "first generation sugars", or are preferably obtained through the treatment and saccharification of non-edible lignocellulosic biomasses, and are therefore defined as "second generation sugars". Lignocellulosic biomasses may be, for example, agricultural residues such as wheat straw or corn stalks, or plants that cannot be used for the food sector such as common reed, fibre sorghum, miscanthus or processing residues of non-edible plants such as guayule, eucalyptus, poplar, or forest residues or processing residues from the papermaking industry. Such mixtures of second generation sugars, which are said hydrolyzates, contain sugars with 5 (C5) and 6 (C6) carbon atoms. Oleaginous yeasts are naturally able to grow on C5 sugars such as xylose and C6 sugars such as glucose, producing cellular biomass and, under particular growth conditions, accumulate lipids in a high percentage with respect to the dry cellular weight.

From the cultivation of said oleaginous yeasts in the bioreactor, a culture broth is obtained including oleaginous cellular biomass to be recovered. Subsequently, the lipids accumulated within the cells must be extracted and separated from the culture broth still present and from the cell debris resulting from appropriate lysis or rupture techniques.

One of the main criticalities in relation to the production of lipids through microbiological methods relates to the fact that the volumetric productivity (i.e. the quantity of lipids to be obtained per unit of volume of culture broth) is limited and, in general, is less than 100 g/L. Consequently, the industrial application of these production processes envisages the use of significant volumes of culture broth of said microorganisms. These large volumes of culture broth must be, of course, treated to recover the resulting oleaginous cellular biomass and proceed with the extraction of the lipids, in large plants, with high set-up and process costs.

For the purpose of guaranteeing the cost effectiveness of the lipid production process, the culture of oleaginous yeasts must reach a high cell density, therefore allowing the productivity of said process to be increased in order to minimize the volume of culture broth and the number of bioreactors used. At the end of growth, the oleaginous cellular biomass obtained must be concentrated in order to reduce the volumes of material to be treated in the subsequent extraction steps of the products obtained (e.g., microbial oils, lipids) and optimize the size of the equipment and volumes of reactants necessary for recovery.

The technical solutions currently used for recovering oleaginous cellular biomass from the culture broth at the end of the growth of the aforesaid oleaginous yeasts are mainly of a physical or chemical nature.

The oleaginous yeasts used for the industrial production of lipids, especially in the case in which they reach high cell density, can lead to culture broths with high viscosity in which the oleaginous cellular biomass obtained is difficult to separate from the aqueous phase, because of its morphological characteristics and the synthesis of substances with surfactant properties. Further, the viscosity of the culture broth makes the cultivation of the oleaginous yeasts in the bioreactor more difficult and costly, because of the lower mixing and oxygenation efficiency of the culture medium. Said criticality is particularly clear in the event that the lipid production process is carried out using oleaginous yeasts that are high lipid producers such as, for example, those belonging to the genus *Trichosporon*.

Commonly, for separating the oleaginous cellular biomass obtained at the end of the lipid production process from the culture broth, techniques are used that imply a difference in density between the two phases of culture broth (i.e. aqueous phase and oleaginous cellular biomass) such as centrifugation, spontaneous sedimentation, hydrocyclones, filtration, filter pressing, microfiltration, ultrafiltration, sometimes continuously coupled to the bioreactor in which said process is carried out. In the event of using oleaginous yeasts belonging to the genus *Trichosporon*, the efficiency of said techniques is, however, very low, because the oleaginous cellular biomass obtained has a very similar density to that of the aqueous phase.

For the purpose of increasing the efficiency, flocculants can be added to the culture broth so as to create cell aggregates that, because of their dimensions, sediment more easily with respect to single cells. However, the addition of flocculants in the proportions prescribed by the prior art has not led to an improvement of the separation of the oleaginous cellular biomass from the aqueous phase. Further, the addition of flocculants can be incompatible with the subsequent lipid extraction processes, because of the high affinity of said flocculants with the solvents used for extraction. In practice, said flocculants could be extracted together with the intracellular lipids and therefore represent impurities to be removed prior to the use of the lipids themselves.

Other methodologies used for the concentration of oleaginous cellular biomass are based on filtration techniques. However, the substances with surfactant properties often produced by oleaginous yeasts hinder the permeation of the aqueous phase through the membrane used for filtration, making the process inefficient.

Methods are also known that envisage the evaporation of excess water such as, for example, heating to induce evaporation, or drying cellular biomass with techniques such as, for example, spray drying or freeze-drying: however, said methods are effective in the concentration of cellular biomass, but require high energy consumption and are not economically feasible for an industrial process for the subsequent production of synthesis intermediates, particularly in the so-called "green chemistry" sector, or in the production of biofuels.

Methods are also known that envisage thermal treatments, at neutral or acidic pH, generally performed after the culture broth has been drained from the bioreactor used in the process for the production of lipids, at the end of said process, so as to make it suitable for centrifuging/filtering and to facilitate the recovery of the oleaginous cellular biomass obtained. However, said methods also require further energy consumptions and, when operating at acidic pH, the neutralization of the acidified waste.

Further, some of the methods described above can lead to the degradation of the cell structures, comprising the characteristics of the final product to be obtained. Finally, the methods described above do not tackle the problem of the viscosity of the culture broth and the consequent increase in energy required due to the need to maintain both good stirring and good oxygenation, within the bioreactor used.

Studies have been performed in order to overcome the aforesaid drawbacks.

For example, international patent application WO 2013/155050 describes an oleaginous microorganism for the production of materials from renewable sources, wherein said microorganism comprises a genetic modification not present in the non-modified microorganism, and wherein said microorganism produces a fermentation broth having a lower viscosity than the one produced by the non-modified microorganism. The aforesaid oleaginous microorganism is said to have a reduced synthesis of exocellular polysaccharides and to be able to produce lipids with high yields.

Since the production of materials from renewable sources, particularly lipids, advantageously usable in the production of synthesis intermediates in the so-called "green chemistry" sector, or in the production of biofuels, is still of great interest, the study of new oleaginous yeasts able to produce lipids with good yields and to be more easily recoverable from the culture broth is also of great interest.

The Applicant therefore set out to solve the problem of identifying an oleaginous yeast able to produce lipids with good yields and more easily recoverable from the culture broth.

The Applicant has now identified a variant of oleaginous yeast able to produce lipids with good yields and more easily recoverable from the culture broth.

In particular, the invention concerns a variant of oleaginous yeast of the species *Trichosporon oleaginosus* filed on May 17, 2017 according to the Budapest Treaty at the Leibniz-Institut DSMZ—Deutsche Sammlung von Mikroorganismen and Zellkulturen GmbH—InhoffenstraBe 7 B 38124 Braunschweig (Germany), deposit number DSM 32508, characterized by mutations affecting the synthesis of the cell wall that modify its morphology with respect to the wild-type strain of the same species. In particular, thanks to said mutations, cell aggregates are formed which, with respect to the wild-type strain of the same species, lower the viscosity of the culture broth, are more easily separable therefrom and thus make their recovery easier. Further, said variant of oleaginous yeast is characterized by yields of oleaginous cellular biomass and intracellular accumulation of lipids that are similar or even higher to those of the wild-type strain.

A further aspect of the present invention relates to a process for the production of lipids through the cultivation of said variant of oleaginous yeast of the species *Trichosporon oleaginosus* DSM 32508.

For the purpose of the present description and of the following claims, the definitions of the numeric ranges always include the extremes unless specified otherwise.

For the purpose of the present description and of the following claims, the term "comprising" also includes the terms "which essentially consists of" or "which consists of".

For the purpose of the present description and of the following claims, the term "biodiesel" means a fuel for diesel engines comprising alkyl esters (e.g., methyl, propyl or ethyl) of long chain fatty acids deriving from biological sources.

For the purpose of the present description and of the following claims, the term "green diesel" means a fuel for diesel engines comprising hydrogenation or deoxygenation products of lipids deriving from biological sources in the presence of hydrogen and of at least one catalyst.

For the purpose of the present description and of the following claims, the expressions "cultivation" and "culture" indicate the processes through which the cells of a microorganism grow and reproduce under human controlled conditions. The processes defined through the above expressions comprise the "culture" of oleaginous yeast, realised in some embodiments of the present invention.

For the purpose of the present description and of the following claims, the expression "culture medium" means a liquid, or a gel, provided to support the growth of the microorganisms, e.g. of the oleaginous yeast cells. The culture medium can be of a defined composition (e.g., "YEPD" medium, "B" medium, etc.) or may derive from the treatment of non-selected sources such as, for example, waste water, market waste, or hydrolyzed lignocellulosic material.

For the purpose of the present description and of the following claims, the expressions "carbon source", "nitrogen source", "sulfur source" and phosphorus source" mean organic or inorganic substances, or compositions of said substances based on carbon, nitrogen, sulfur (e.g., sulfates) and phosphorus (e.g., phosphates), respectively, contained in the culture medium and that a microorganism can metabolize for deriving energy.

For the purpose of the present description and of the following claims, the term "biomass" means the assembly of cells produced during the process for the production of lipids according to the present invention or in the other culture methods.

Further characteristics and advantages of the present invention will become clear from the following detailed description.

Therefore, the subject matter of the present invention is constituted by a variant of oleaginous yeast of the species *Trichosporon oleaginosus* filed on May 17, 2017 according to the Budapest Treaty at the Leibniz-Institut DSMZ—Deutsche Sammlung von Mikroorganismen and Zellkulturen GmbH—InhoffenstraBe 7 B 38124 Braunschweig (Germany), deposit number DSM 32508.

The genotype of the variant of oleaginous yeast of the species *Trichosporon oleaginosus* DSM 32508 was characterized by comparing the sequence of its genomic DNA with that of the wild-type strain of oleaginous yeast *Trichosporon oleaginosus* ATCC 20509 as described in Example 4 reported below.

The genome of the wild-type strain of oleaginous yeast of the species *Trichosporon oleaginosus* ATCC 20509 has a size of 19601063 base pairs (bps) and contains 8283 genes. Of these, 3621 genes have been identified with a known function and 4419 genes have been annotated. From the comparison with the genome of the variant of oleaginous yeast of the species *Trichosporon oleaginosus* DSM 32508 a total of 647 mutations have been highlighted, 228 of which are homozygous and 420 heterozygous.

The mutations affecting the coding regions are described below which, directly or indirectly, lead to a modification of the amino acid sequence of the proteins coded by the gene in which each mutation is found. In particular, the proteins involved in the cell wall synthesis process are analysed, whose modification can affect the cell morphology, the viscosity characteristics of the culture broth and the ease of sedimentation of the yeast cells present in said culture broth. More in particular, there were a total of 131 mutations of the coding regions that lead to a modification of the amino acid sequence of the corresponding protein. Of the latter, 22 are by deletion, 13 by insertion, 89 by single nucleotide variation (SNV) and 3 by multiple nucleotide variation (MNV). 30 homozygous mutations (discovered in genes present in a single copy) were identified. Of these, in particular a deletion mutation results in a gene whose protein is associated with components of the wall, in particular chitin, and that therefore, without wishing to refer to any theory, could be correlated with the phenotype of different morphology of the variant of oleaginous yeast of the species *Trichosporon oleaginosus* DSM 32508 and determine its greater sedimentation facility (centrifugability). In fact, deletion mutation causes the lack of synthesis of a protein with chitin synthase activity (annotated by homology as chitin synthase 4 of the yeast *Saccharomyces cerevisiae*), thus preventing the correct production of chitin, necessary for the formation of a complete cell wall. In fact, variants of *Saccharomyces cerevisiae* yeast that present mutations in the synthesis of the chitin show defects in the separation of the daughter cells from the mother cells, hence generating groups of unseparated cells. Further, the cells show a different shape and size compared to those of the wild-type strain as reported, for example, in: Bulawa C. E., "*Annual Review of Microbiology*" (1993), Vol. 47, pag. 505-534; Cabib E. et al, "*Nature Reviews Microbiology*" (2013), Vol. 11, pag. 648-655.

269 heterozygous mutations (found in genes present in more than one copy) were identified in coding regions for proteins, 92 of which being in genes coding for proteins whose function is known. Of these, three mutations affected genes whose protein is associated with components of the cell wall or membrane, and therefore potentially involved in alterations of their morphological and functional characteristics. In particular, a deletion mutation regards the gene coding for a putative membrane lipoprotein. The second mutation, by single nucleotide variation (SNV) which produces the change of a single amino acid in the protein affects the gene coding an enzyme involved in the biosynthesis of N-acetylglucosaminyl-phosphatidylinositol (GlcNAc-PI), the first intermediate in the "pathway" of the "GPI anchor", i.e. the glycolipid that is needed to anchor the proteins to the cell wall. The third mutation, also by single nucleotide variation (SNV), relates to the gene coding for a protein with chitin synthase activity, and therefore involved in the synthesis of chitin (annotated by homology as chitin synthase 1 of the yeast *Saccharomyces cerevisiae*). Also in this case, without wishing to refer to any theory, all of said mutations, even heterozygous, but associated with homozygous mutation affecting the synthesis of chitin, could be correlated with the phenotype of different morphology of the variant of oleaginous yeast of the species *Trichosporon oleaginosus* DSM 32508 and determine profound alterations in the structure of the cell wall, generating cell aggregates that are more easily separable from the aqueous phase of the culture broth.

The following Table 1 and Table 2 show mutations detected in the genomic DNA of the variant of oleaginous yeast of the species *Trichosporon oleaginosus* DSM 32508 (Mutant) with respect to the wild-type strain (Wild-type), that lead to the change in protein sequence. For each mutation, the position on the so-called "scaffold" is indicated, i.e. on one of the contiguous regions of genomic DNA that, assembled based on their nucleotide sequence, allow the reconstruction of the genome. Table 1 and Table 2 also indicate: the type of mutation: SNV "single nucleotide variation", i.e. mutation of single nucleotide; MNV: "multiple nucleotide variation", i.e. mutation of various nucleotides in sequence; Insertion of one or more nucleotides; Deletion of one or more nucleotides; the number of nucleotides involved, the nucleotide or nucleotides varied (by mutation, insertion or deletion) respectively in the genome of the wild-type strain and in the genome of the variant of oleaginous yeast DSM 32508. The homozygous mutations are those found in genes present in a single copy in the genome (Table 1); heterozygous mutations are those found in genes present in various copies in the genome (Table 2).

TABLE 1

| Scaffold | Position | Type | Length | Wild-type | Mutant | Annotation |
|---|---|---|---|---|---|---|
| scaffold102_size41884 mapping | 2776 | Deletion | 4 | GGTC | — | Transcription factor |
| scaffold1042_size9002 mapping | 457 | Deletion | 2 | GT | — | CHS4-Chitin synthase 4 |
| scaffold1067_size4903 mapping | 387 | Insertion | 1 | — | C | PRP45 Pre-mRNA-processing protein 45 |
| | 388 | Insertion | 1 | — | C | |
| | 398 | Insertion | 1 | — | G | |
| | 399 | SNV | 1 | T | A | |
| | 384 | SNV | 1 | T | C | |
| scaffold1115_size6086 mapping | 4180 | SNV | 1 | G | T | PFS2-Polyadenylation factor subunit 2 |
| scaffold1135_size4105 mapping | 23 | SNV | 1 | G | A | ssn6-General transcriptional corepressor |
| scaffold1157_size4327 mapping | 386 | Insertion | 9 | — | CCATACCCA | AO-I-Copper amine oxydase 1 |
| scaffold125_size33269 mapping | 28060 | Insertion | 1 | — | T | mam4-Protein-S-isoprenylcysteine O-methyltransferase |
| scaffold128_size27785 mapping | 910 | Deletion | 2 | CC | — | DOLPP1-Dolichol diphosphatase 1 |
| scaffold133_size33047 mapping | 616 | SNV | 1 | G | A | SEC62 |
| | 624 | Deletion | 3 | ACT | — | |
| scaffold1330_size2886 mapping | 2852 | MNV | 3 | TCG | AGC | klp1-Kinesin heavy chain |
| scaffold14_size55374 mapping | 8058 | SNV | 1 | T | C | TOP3A-Topoisomerase |
| | 8054 | SNV | 1 | A | C | |
| scaffold1522_size3854 mapping | 3108 | SNV | 1 | A | G | Tf2-1_3-Retrotransposable element |
| | 2376 | SNV | 1 | A | C | |
| | 2388 | SNV | 1 | T | G | |
| | 1697 | SNV | 1 | A | G | |
| | 1307 | SNV | 1 | A | G | |
| | 3035 | Deletion | 5 | GCGGG | — | |
| scaffold1543_size2681 mapping | 633 | Insertion | 2 | — | TG | usp30-Ubiquitin carboxyl-terminal hydrolase |
| scaffold1590_size4460 mapping | 1776 | Deletion | 4 | CGTC | — | Putative nitronate monooxygenase |
| scaffold1613_size1563 mapping | 1518 | Deletion | 1 | G | — | PBP2-Polyadenylation regulator |
| scaffold1641_size2263 mapping | 1537 | Deletion | 10 | TTTGTGGTTA | — | Carbonic anhydrase |
| scaffold1648_size10529 mapping | 7108 | Deletion | 10 | TGTTGGTGTT | — | MIDI-Ca+ influx, stress resistance |
| scaffold176_size44024 mapping | 23633 | Deletion | 5 | AACGA | — | RPS16-40S ribosomal protein S16 |
| scaffold1772_size2790 mapping | 1425 | Deletion | 6 | CCGCCC | — | paaF-Enoyl-CoA hydratase, fatty acid beta oxidation |
| scaffold1833_size2599 mapping | 831 | Insertion | 1 | — | G | Strn4-Signal transduction |
| | 1323 | Deletion | 1 | C | — | |
| | 982 | Deletion | 6 | ACCTGT | — | |
| scaffold214_size32099 mapping | 542 | Deletion | 1 | T | — | cbc1-Cap-binding protein subunit 1 |
| scaffold260_size19451 mapping | 18650 | Deletion | 3 | GGG | — | SAS10-involved in the nucleolar processing of pre-18S |
| scaffold261_size19295 mapping | 708 | Deletion | 5 | CAGGA | - | NPRL2-Nitrogen permease regulator 2-like protein |
| scaffold265_size18389 mapping | 12923 | SNV | 1 | T | C | NSP1_2-Nucleoporin |
| scaffold306_size31322 mapping | 2060 | SNV | 1 | N | T | hibA-putative 3-hydroxyisobutyrate |

TABLE 1-continued

| Scaffold | Position | Type | Length | Wild-type | Mutant | Annotation |
|---|---|---|---|---|---|---|
| | | | | | | dehydrogenase |
| scaffold387_size17704 mapping | 2359 | Deletion | 8 | GGGCTCGC | — | rnr-1-Ribonucleoside diphosphate reductase large chain |

TABLE 2

| Scaffold | Position | Type | Length | Wild-type | Mutant | Annotation |
|---|---|---|---|---|---|---|
| scaffold10_size59962 mapping | 17910 | SNV | 1 | T | C | nim-1 - G2 specific protein kinase |
| scaffold105_size30064 mapping | 1861 | SNV | 1 | C | T | tea1 - Tip elongation aberrant protein |
| scaffold1069_size4474 mapping | 2070 | Insertion | 1 | — | G | HHT1 - Histone H3 |
| scaffold1115_size6086 mapping | 4171 | SNV | 1 | C | T | PFS2 - Polyadenylation factor subunit |
| | 4168 | SNV | 1 | T | C | |
| scaffold1201_size4291 mapping | 434 | SNV | 1 | T | C | oca2 - Serine/threonine protein kinase |
| scaffold1270_size3209 mapping | 1895 | SNV | 1 | A | G | scd2 |
| scaffold128_size27785 mapping | 18900 | SNV | 1 | G | A | Gene: Ca-P60A, CDS: Ca-P60A |
| scaffold1296_size6178 mapping | 1412 | SNV | 1 | C | T | Tf2-1_1 - Retrotransposable element |
| | 590 | SNV | 1 | C | A | |
| | 860 | SNV | 1 | G | A | |
| | 1986 | SNV | 1 | T | C | |
| | 2841 | SNV | 1 | T | C | |
| | 2778 | SNV | 1 | T | A | |
| | 2829 | SNV | 1 | T | C | |
| | 2370 | Insertion | 1 | — | A | |
| | 485 | SNV | 1 | T | C | |
| | 486 | SNV | 1 | T | C | |
| | 1250 | SNV | 1 | T | C | |
| | 3063 | SNV | 1 | C | T | |
| | 1308 | SNV | 1 | T | C | |
| scaffold1399_size2575 mapping | 67 | SNV | 1 | T | C | nuo-21_1 |
| scaffold14_size55374 mapping | 17423 | SNV | 1 | G | A | his-6 |
| scaffold14_size55374 mapping | 8060 | Insertion | 1 | — | G | TOP3A - DNA topoisomerase 3-alpha |
| scaffold141_size26007 mapping | 21392 | SNV | 1 | G | T | PXA1 - Peroxisomal long chain fatty acid import protein |
| scaffold145_size25803 mapping | 20568 | SNV | 1 | T | C | Etnppl |
| scaffold1450_size3468 mapping | 2277 | Insertion | 1 | — | G | dnaJ |
| | 2281 | MNV | 2 | CA | GC | |
| scaffold148_size25263 mapping | 9938 | SNV | 1 | T | A | NUP205 - Nuclear pore complex protein |
| scaffold1522_size3854 mapping | 585 | SNV | 1 | A | G | Tf2-1_3 - Retrotransposable element |
| | 3276 | SNV | 1 | A | T | |
| | 3219 | SNV | 1 | T | C | |
| | 2310 | SNV | 1 | T | C | |
| | 3536 | SNV | 1 | C | T | |
| | 3282 | SNV | 1 | G | T | |
| | 2629 | SNV | 1 | A | T | |
| | 3290 | SNV | 1 | A | G | |
| | 3093 | SNV | 1 | T | C | |
| | 1739 | SNV | 1 | T | C | |
| | 3542 | SNV | 1 | A | G | |
| | 3404 | SNV | 1 | G | A | |
| | 3120 | SNV | 1 | T | C | |
| | 3051 | SNV | 1 | T | C | |
| | 633 | SNV | 1 | C | G | |
| | 1872 | SNV | 1 | C | T | |
| scaffold160_size33150 mapping | 20209 | SNV | 1 | T | C | pom152 - Nucleoporin |
| scaffold162_size23983 mapping | 21006 | SNV | 1 | T | A | DBP10 - ATP-dependent RNA helicase |
| scaffold1620_size1538 mapping | 1141 | SNV | 1 | T | C | PEG10_1 - Retrotransposon derived protein |
| scaffold1666_size3720 mapping | 1453 | SNV | 1 | G | A | RPL7 - 60S ribosomal protein L7 |
| scaffold17_size51795 mapping | 43619 | SNV | 1 | C | T | Mmel1 membrane metal-endopeptidase-like 1 |
| scaffold189_size23947 mapping | 18523 | Insertion | 1 | — | G | mtr_3 - Amino acid transporter |
| scaffold1925_size4739 mapping | 339 | SNV | 1 | C | T | Elmo1 - Actin cytoskeleton organizer |
| scaffold195_size22323 mapping | 19547 | SNV | 1 | T | C | LAC12 2 - sugar permease |
| scaffold197_size21962 mapping | 10998 | SNV | 1 | A | G | tra1 - Transcription associated protein |
| | 10347 | SNV | 1 | C | T | |
| | 14540 | SNV | 1 | T | C | |
| scaffold201_size22232 mapping | 15379 | SNV | 1 | A | G | prp43 - RNA helicase |
| scaffold2026_size1526 mapping | 320 | SNV | 1 | G | A | HD-10 - homeo-box |
| scaffold205_size21540 mapping | 8038 | SNV | 1 | T | C | LIP4_2 - lipase |
| scaffold209_size21982 mapping | 16765 | SNV | 1 | C | T | ADE2 -adenine pathway |
| scaffold214_size32099 mapping | 533 | SNV | 1 | C | G | cbc1 - CAP binding complex |
| | 536 | SNV | 1 | C | T | (important in the response to osmotic stress) |
| | 543 | Insertion | 4 | — | ACGG | |
| scaffold215_size30252 mapping | 11090 | SNV | 1 | A | G | LAC - Laccase |

TABLE 2-continued

| Scaffold | Position | Type | Length | Wild-type | Mutant | Annotation |
|---|---|---|---|---|---|---|
| scaffold217_size20594 mapping | 1566 | SNV | 1 | G | A | NCBP - Translation initiation factor |
| scaffold220_size20471 mapping | 9293 | MNV | 2 | AG | GA | RKI1 - Ribose-5P isomerase |
| scaffold222_size20448 mapping | 18981 | SNV | 1 | G | A | pkiA - Pyruvate kinase |
| scaffold25_size49612 mapping | 20734 | SNV | 1 | A | G | Rangrf - Guanine nucleotide releasing factor |
| scaffold252_size21098 mapping | 12958 | Deletion | 1 | G | — | VMS1 - Component of a Cdc48p complex involved in protein quality control; exhibits cytosolic and ER membrane localization |
| scaffold255_size18966 mapping | 4684 | SNV | 1 | A | G | PIGS - biosynthesis of phosphatidylinositol glycan anchor |
| scaffold260_size19451 mapping | 4761 | Deletion | 2 | GA | — | Putative ankyrin-containing lipoprotein involved in the integrity of the membrane |
| scaffold27_size49090 mapping | 46386 | SNV | 1 | A | G | str3_5 - Siderophore iron carrier |
| scaffold280_size17908 mapping | 5817 | Deletion | 1 | C | — | sks2 - heat shock protein |
|  | 6351 | Deletion | 1 | A | — |  |
| scaffold305_size17341 mapping | 6313 | SNV | 1 | T | C | lsg1 - Large subunit GTPase 1 |
| scaffold31_size47703 mapping | 35375 | SNV | 1 | G | T | MCH4_2 - Monocarboxylate permease |
| scaffold317_size16538 mapping | 9719 | SNV | 1 | T | A | CAND1 |
| scaffold324_size16216 mapping | 9262 | SNV | 1 | C | T | cut6 |
| scaffold341_size15653 mapping | 6256 | SNV | 1 | T | G | CHS1 - Chitin synthase 1 |
| scaffold347_size15416 mapping | 6346 | SNV | 1 | C | T | rfbB - Glucose 4,6 dehydratase |
| scaffold35_size48345 mapping | 36831 | SNV | 1 | G | A | not2 - RNA polymerase regulator |
| scaffold353_size15157 mapping | 1529 | SNV | 1 | T | A | mutS - Meiotic recombination |
| scaffold354_size19402 mapping | 12608 | SNV | 1 | G | C | rrp14c - Ribosomal RNA processing |
| scaffold370_size23342 mapping | 11273 | SNV | 1 | G | A | hdhA - Hydroxysteroid dehydrogenase |
| scaffold370_size23342 mapping | 8884 | Deletion | 1 | C | — | KDM3A - Lysine demethylase |
| scaffold377_size14372 mapping | 1170 | SNV | 1 | T | C | ERT1_1 - Activator of gluconeogenesis |
| scaffold378_size14357 mapping | 7892 | SNV | 1 | T | C | smd2 - Ribonucleoprotein |
| scaffold385_size14962 mapping | 13792 | SNV | 1 | C | A | MEF1 - Mitochondrial elongation factor |
| scaffold39_size43714 mapping | 35715 | SNV | 1 | T | G | APL4 - Vesicular transport |
| scaffold391_size16428 mapping | 2575 | SNV | 1 | A | G | sce3 - Translation initial factor |
| scaffold40_size47628 mapping | 33362 | SNV | 1 | G | A | HSP31 - Heat shock protein |
| scaffold403_size14321 mapping | 6958 | SNV | 1 | C | T | IWS1 - Transcription elongation factor |

The modification of the cell morphology of the variant of oleaginous yeast of the species *Trichosporon oleaginosus* DSM 32508, compared with the wild-type strain, was verified in various experiments, some of which are described in the examples provided below, wherein said modification was detected both under an optical microscope and through flow cytofluorimetry. Further, the production of biomass and the quantity of lipids accumulated during the lipid production process according to the present invention were determined. Finally, the viscosity and centrifugability (i.e., the concentration factor) of the culture broth obtained from said process at different times from inoculation were determined.

The variant of oleaginous yeast of the species *Trichosporon oleaginosus* DSM 32508 object of the present invention was obtained through a mutagenesis process carried out by exposing cells of the wild-type strain of oleaginous yeast of the species *Trichosporon oleaginosus* ATCC 20509 to ultraviolet (UV) radiation with wavelength ranging from 230 nm to 260 nm. Mutagenesis by exposure to UV radiation can be carried out according to the prior art as described, for example, in Winston F. et al, "*Current Protocols in Molecular Biology*" (2008), DOI:10.1002/0471142727.mb1302s82, John Wiley & Sons. For example, said mutagenesis can be performed by exposing the cells of the wild-type strain of oleaginous yeast of the species *Trichosporon oleaginosus* ATCC 20509 placed in a Petri dish on medium solidified with agar to a source of UV radiation (represented by at least one lamp with power ranging from 8 Watt to 15 Watt, with wavelength ranging from 230 nm to 260 nm), placed at a distance from the Petri dish ranging from 10 cm to 50 cm, for a time ranging from 5 seconds to 5 minutes.

As mentioned above, the present invention also relates to a process for the production of lipids through the cultivation of said variant of oleaginous yeast of the species *Trichosporon oleaginosus*.

Therefore, further subject matter of the present invention is a process for the production of lipids comprising:
preparing an inoculum comprising at least one variant of oleaginous yeast of the species *Trichosporon oleaginosus* DSM 32508;
feeding said inoculum to a culture device obtaining a culture broth;
subjecting said culture broth to separation obtaining an aqueous suspension of a concentrated oleaginous cellular biomass comprising lipids and an aqueous phase;
extracting the intracellular lipids accumulated inside the yeast cells.

For the purpose of the process according to the present invention, said culture device may be, for example, a bioreactor and said separation may be carried out, for example, through centrifugation.

In accordance with a preferred embodiment of the present invention, said process can be carried out at a temperature ranging from 10° C. to 40° C., preferably ranging from 20° C. to 35° C.

In accordance with a preferred embodiment of the present invention, said process can be carried for a time ranging from 40 hours to 200 hours, preferably ranging from 80 hours to 150 hours.

In accordance with a preferred embodiment of the present invention, said process can be carried under aerobic conditions.

Said aerobic conditions can be actuated, for example, by insufflating sterile air into the culture device and through variable agitation, said agitation depending on the type of culture device used.

In accordance with a preferred embodiment of the present invention, said process can be carried out at a pH ranging from 4.5 to 7.0, preferably ranging from 5.0 to 6.5. For the purpose of maintaining the pH in the desired ranges, an aqueous solution can be added to the culture medium of at least one inorganic base, for example, sodium hydroxide (NaOH), potassium hydroxide (KOH), calcium dihydroxide [Ca(OH)$_2$], magnesium hydroxide [Mg(OH)$_2$], or mixtures thereof, preferably potassium hydroxide (KOH), or an aqueous solution of at least one inorganic acid such as, for example, phosphoric acid (H$_3$PO$_4$), sulfuric acid (H$_2$SO$_4$), hydrochloric acid (HCl), or mixtures thereof, preferably sulfuric acid (H$_2$SO$_4$), in quantities such as to obtain the desired pH.

In accordance with a preferred embodiment of the present invention, said process may be carried out starting from an inoculum in an amount ranging from 1% to 5% (vol/vol) of the total volume of culture medium, obtained from a previous culture of said variant of oleaginous yeast of the species *Trichosporon oleaginosus* DSM 32508, carried out in the same culture medium for a time ranging from 6 hours to 24 hours.

Said previous culture can in turn be inoculated by an anterior culture, or can be inoculated starting from a sample of said variant of oleaginous yeast of the species *Trichosporon oleaginosus* DSM 32508, maintained at −80° C. in suspension containing 15% (vol/vol) glycerol.

In accordance with a preferred embodiment of the present invention, said process can be carried out in a culture medium comprising glucose as carbon source and ammonium sulfate [(NH$_4$)$_2$SO$_4$] as nitrogen source.

In accordance with a preferred embodiment of the present invention, said process can be carried out in fed-batch.

In accordance with a preferred embodiment of the present invention, said process, after a time ranging from 15 hours to 25 hours after the inoculation, can be further carried out in fed-batch, preferably for a time ranging from 25 hours to 175 hours, more preferably ranging from 65 hours to 125 hours, by adding a further nitrogen source such as, for example corn steep liquor, yeast extract, ammonium sulfate, urea, in such an amount as to add to the culture broth a total quantity of nitrogen ranging from 0.5 g/L to 5 g/L.

In accordance with a preferred embodiment of the present invention, said process, after a time ranging from 15 hours and 25 hours after the inoculation, can be further carried out in fed-batch, preferably for a time ranging from 25 hours to 175 hours, more preferably ranging from 65 hours to 125 hours, by adding an aqueous solution of glucose so as to have a constant concentration of glucose in the culture broth ranging from 25 g/L to 50 g/L.

The cell growth during the culture can be measured by spectrophotometric methods determining the turbidity, or optical density (OD) of a sample of culture broth at 660 nm (OD$_{660}$).

At the end of the aforesaid process, the cells of the variant of oleaginous yeast of the species *Trichosporon oleaginosus* DSM 32508 used, can be separated from the culture broth through methods known in the state of the art such as, for example, filtration, filter pressing, microfiltration or ultrafiltration, centrifugation, preferably by centrifugation. Preferably, said centrifugation can be carried out for a time ranging from 5 minutes to 30 minutes, preferably ranging from 15 minutes to 25 minutes, at a rotation speed ranging from 3000 rpm to 9000 rpm, preferably ranging from 4000 rpm to 8000 rpm. It is to be noted that the operating conditions indicated for centrifugation relate to a process carried out on laboratory scale: in the case of an industrial process, in which generally continuous centrifuges are used, the person skilled in the art will be able to adapt said operating conditions.

The concentration of oleaginous cellular biomass obtained can be measured in grams per litre of culture broth, determining the dry weight of the cells of oleaginous yeast of a sample of culture broth of a known volume taken at preset intervals and at the end of said process. In particular, "dry weight" of oleaginous cellular biomass means the weight of the cells contained in a known volume of culture broth, determined by weighing the aforesaid cells after removing all the water content through a heat treatment in a ventilated oven at 105° C. up to constant weight (about 24 hours).

For the purpose of recovering lipids, the oleaginous cellular biomass obtained can be subjected to cell lysis according to processes known in the state of the art and described, for example, in international patent application WO 2014/102254 including, for example, thermal treatment in a pressurized reactor, mechanical treatment with a homogenizer, or microwave treatment.

At the end of said cell lysis, the lipids can be recovered from the suspension obtained, through extraction with polar or non-polar organic solvents, according to processes known in the state of the art and described, for example, in international patent application WO 2014/102254.

The production of lipids by the oleaginous yeasts at the end of the process object of the present invention can be measured with colorimetric methods known in the state of the art, directly in samples of suspensions of yeast cells, for example with sulpho-phospho vanilline using, for example, the kit "Total lipids—sulpho-phospho vanilline" sold by Spinreact S.A.U., Ctra. Santa Coloma, 7 E-17176 St. Esteve d'en Bas (GI), Spain.

Further, the quantity of lipids produced can be determined with gravimetric methods on the fraction extracted with mixtures of organic solvents, for example with chloroform: methanol 2:1, vol/vol as described in Folch J. et al, "*The Journal of Biological Chemistry*" (1957), vol. 226, pag. 497-509; or extracted with n-hexane:isopropanol 3:2 vol/vol as described in Hara A. et al, "*Analytical Biochemistry*" (1978), Vol. 90, pag. 420-426, from samples of freeze-dried biomass.

Therefore, to evaluate the performance in relation to the accumulation of lipids, in the process object of the present invention, of the variant of oleaginous yeast of the species *Trichosporon oleaginosus* DSM 32508, with respect to the wild-type strain, in the following examples, the dry weight of biomass (expressed in g/L) and the quantity of lipids (expressed in g/L) were determined with the methods listed above at the end of said process and the percentage ratio between these two parameters was calculated.

It is to be noted that, operating according to the process object of the present the invention, the variant of the species *Trichosporon oleaginosus* DSM 32508, with respect to the wild-type strain of the same species, allows an increase in productivity of up to 50% and an increase in the lipid titer of up to 70% to be obtained.

It is also to be noted that, operating according to the process object of the present invention, the culture broth obtained at the end of said process with the variant of oleaginous yeast of the species *Trichosporon oleaginosus* DSM 32508, with an equivalent concentration of oleaginous yeast cells and lipid content, has a viscosity from 2 to 10 times lower, with respect to the viscosity of culture broth obtained with the wild-type strain of oleaginous yeast of the species *Trichosporon oleaginosus* ATCC 20509, performed under the same operating conditions.

The lipid fraction was analysed through chromatographic techniques, for example by gas chromatography or by high performance liquid chromatography (HPLC) according to processes known in the prior art.

Through said analytical methods it was detected that the lipids accumulated in the oleaginous yeast cells, both of the variant and of the wild-type strain, are 90% represented by triglycerides, preferably esters of glycerol with fatty acids having from 8 to 24 carbon atoms, such as, for example, palmitic acid, stearic acid, oleic acid and α-linoleic acid.

Other lipids that can be present are: phospholipids, monoglycerides, diglycerides, free fatty acids, or mixtures thereof.

The lipids obtained according to the process object of the present invention can be advantageously used as synthesis intermediates, particularly in the so-called "green chemistry" sector. Further, they can be subjected to transesterification in the presence of at least one alcohol having from 1 to 4 carbon atoms, preferably methanol or ethanol, and at least one acidic or basic catalyst, in order to produce glycerol and alkyl esters, in particular methyl esters or ethyl esters ("biodiesel").

Alternatively, said lipids can be subjected to hydrogenation/deoxygenation in the presence of hydrogen and at least one catalyst in order to produce "green diesel". Hydrogenation/deoxygenation processes are known in the prior art and are described, for example, in European patent application EP 1,728,844.

For the purpose of putting the present invention into practice and illustrating it more clearly, below are some non-limiting examples.

EXAMPLE 1 (Obtaining the Variant of Oleaginous Yeast of the Species *Trichosporon oleaginosus* DSM 32508)

An example of the application of the method of obtaining variants of the wild-type strain of the species *Trichosporon oleaginosus* ATCC 20509 is provided below, which led to obtaining the variant of oleaginous yeast of the species *Trichosporon oleaginosus* filed at the Leibniz-Institut DSMZ, with deposit number DSM 32508. In this example, casual mutagenesis was obtained through UV radiation.

For this purpose a sample of cells of a wild-type strain of oleaginous yeast of the species *Trichosporon oleaginosus* ATCC 20509 was inoculated in a flask containing "YEPD" medium (yeast extract 10 g/L, peptone 10 g/L, glucose 20 g/L): the flask was placed in an agitated incubator, at 30° C., for one night. Subsequently, the cells were collected through centrifugation at 4000 rpm for 5 minutes, washed in sterile water, then diluted 1:10 in sterile water and plated on Petri dishes containing a solid lipogenesis "B" medium (agar 20 g/L, glucose 50 g/L, ammonium sulfate $[(NH_4)_2SO_4]$ 1 g/L, yeast extract 1 g/L, potassium dihydrogen phosphate $[KH_2PO_4]$ 1 g/L, magnesium sulfate heptahydrate $[MgSO_4.7H_2O]$ 0.05 g/L, sodium chloride [NaCl] 0.01 g/L, calcium chloride dihydrate $[CaCl_2.2H_2O]$ 0.01 g/L) so as to have about 100 colonies per plate.

The plates were exposed to a source of ultraviolet radiation, represented by a 15 Watt UV lamp (wavelength 254 nm), placed at a distance of 10 cm, for a time equal to 40 seconds, so as to obtain a residual vitality rate of 10%. Subsequently, the plates were incubated at 30° C., for 4 days, until the colonies reached a sufficient size to be counted. After mutagenesis a colony was selected with irregular and jagged edges corresponding to a variant of oleaginous yeast of the species *Trichosporon oleaginosus* DSM 32508 which was plated again on Petri dishes containing the aforesaid solid lipogenesis "B" medium.

Figure 1:
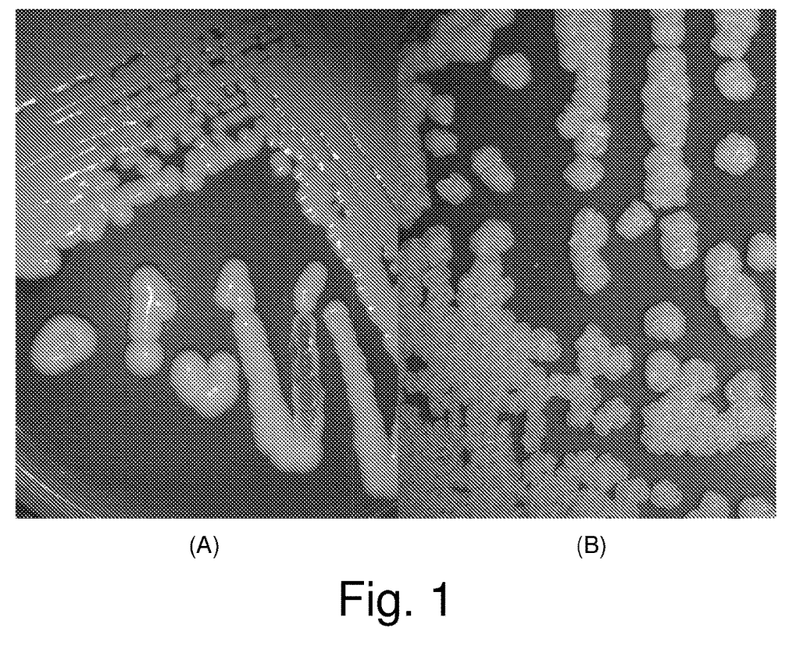
FIG. 1A: a photo of a Petri dish that had not been exposed to mutagenesis in which it can be seen that the colonies of the wild-type strain of oleaginous yeast of the species of *Trichosporon oleaginosus* ATCC 20509 have a round shape and a glossy and mucous appearance.
FIG. 1B a photo of a Petri dish in which it can be seen that the colonies of the variant of oleaginous yeast of the species *Trichosporon oleaginosus* DSM 32508 have irregular and jagged edges and a non-glossy appearance.

For comparative purposes, some dishes were not exposed to mutagenesis. FIG. 1 shows:

(A): a photo of a Petri dish that had not been exposed to mutagenesis in which it can be seen that the colonies of the wild-type strain of oleaginous yeast of the species *Trichosporon oleaginosus* ATCC 20509 have a round shape and a glossy and mucous appearance;

(B) a photo of a Petri dish in which it can be seen that the colonies of the variant of oleaginous yeast of the species *Trichosporon oleaginosus* DSM 32508 have irregular and jagged edges and a non-glossy appearance.

EXAMPLE 2 (Modification of the Cell Morphology of the Variant of Oleaginous Yeast of the Species *Trichosporon oleaginosus* DSM 32508: Observation Under the Optical Microscope)

The morphological diversity between cells of a wild-type strain of oleaginous yeast of the species *Trichosporon oleaginosus* ATCC 20509 and cells of the variant of oleaginous yeast of the species *Trichosporon oleaginosus* DSM 32508 was evaluated using an optical microscope.

For this purpose a sample of cells of a wild-type strain of oleaginous yeast of the species *Trichosporon oleaginosus* ATCC 20509 and a sample of cells of the variant of oleaginous yeast of the species *Trichosporon oleaginosus* DSM 32508 were inoculated, in two different flasks, in "YEPD" medium (yeast extract 10 g/L, peptone 10 g/L, glucose 20 g/L): the flasks were placed in an agitated incubator, at 30° C., for one night. Subsequently, from each flask, an aliquot of culture broth was taken, placed on a slide and observed under the optical microscope with an enlargement of 400× (FIG. 2).

Figure 2:
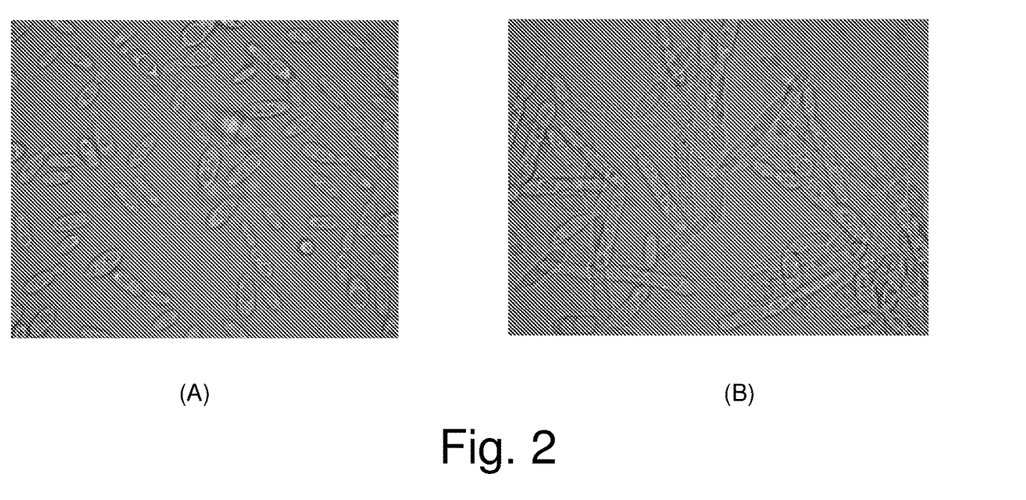
FIGS. 2A and 2B show results from Example 2 as to morphological diversity between cells of a wild-type strain of oleaginous yeast of the species *Trichosporon oleaginosus* ATCC 20509 and cells of the variant of oleaginous yeast of the species *Trichosporon oleaginosus* DSM 32508 using an optical microscope.

From FIG. 2 it can be observed that:

(A): the cells of the wild-type strain of oleaginous yeast of the species *Trichosporon oleaginosus* ATCC 20509 are oval shaped or slightly elongated, are in the active reproduction phase and the buds separate correctly at the end of the budding process;

(B): the cells of the variant of oleaginous yeast of the species *Trichosporon oleaginosus* DSM 32508 are very elongated and do not correctly conclude the budding process and tend to form aggregates.

Subsequently, an aliquot of cells coming from each of the previous cultures was transferred, into two different flasks, in liquid lipogenesis "B" medium (glucose 50 g/L, ammonium sulfate $[(NH_4)_2SO_4]$ 1 g/L, yeast extract 1 g/L, potassium dihydrogen phosphate $[KH_2PO_4]$ 1 g/L, magnesium sulfate heptahydrate $[MgSO_4.7H_2O]$ 0.05 g/L, sodium chloride [NaCl] 0,01 g/L, calcium chloride dihydrate $[CaCl_2.2H_2O]$ 0.01 g/L), so as to obtain a cell density of 0.1 $OD_{660}$/mL: the flasks were placed in an agitated incubator, at 30° C., for 96 hours. Subsequently, from each flask, an aliquot of culture broth was taken, placed on a slide and observed under the optical microscope with an enlargement of 400× (FIG. 3).

Figure 3:
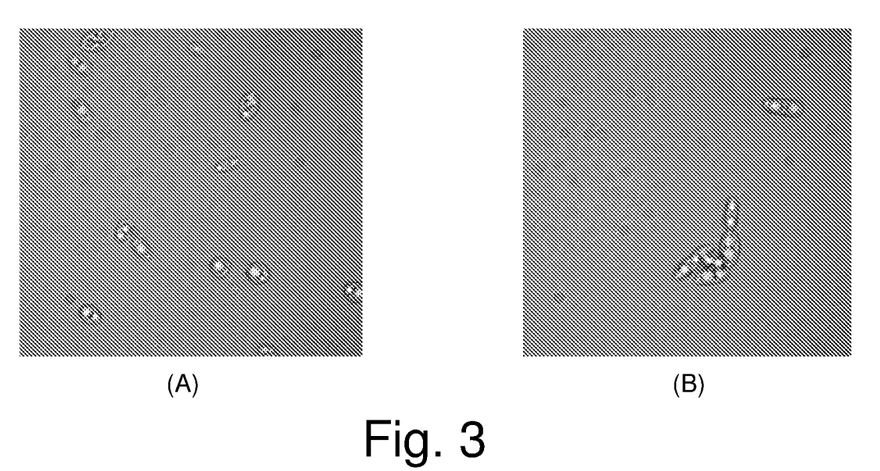
FIGS. 3A and 3B show results from Example 2 under the optical microscope with an enlargement of 400X.

From FIG. 3 it can be observed that:

(A): the cells of the wild-type strain of oleaginous yeast of the species *Trichosporon oleaginosus* ATCC 20509 have a roundish shape and appear as single cells;

(B): the cells of the variant of oleaginous yeast of the species *Trichosporon oleaginosus* DSM 32508 are more elongated and tend to form doublets and aggregates.

EXAMPLE 3 (Modification of the Cell Morphology of the Variant of Oleaginous Yeast of the Species *Trichosporon oleaginosus* DSM 32508: Study Through Flow Cytofluorimetry)

The morphological diversity between cells of a wild-type strain of oleaginous yeast of the species *Trichosporon ole-*

*aginosus* ATCC 20509 and cells of the variant of oleaginous yeast of the species *Trichosporon oleaginosus* DSM 32508, was analyzed qualitatively and quantitatively at single cell level through flow cytofluorimetry. Said analysis was carried out as stated in: Gunasekera T. S. et al, "*International Journal of Food Microbiology*" (2003), Vol. 85, Issue 3, pag. 269-279; Cronin U. P. et al, "*Journal of Applied Microbiology*" (2010), Vol. 108, Issue 1, pag. 1-16. The flow cytofluorimeter used (BD Accuri C6 plus) was equipped with an argon ion laser that emits at 488 nm. The measurements was performed on a total of 20000 events with an acquisition flow of the sample equal to 35 µl/min.

For this purpose a sample of cells of a wild-type strain of oleaginous yeast of the species *Trichosporon oleaginosus* ATCC 20509 and a sample of cells of the variant of oleaginous yeast of the species *Trichosporon oleaginosus* DSM 32508 were inoculated, in two different flasks, in "YEPD" medium (yeast extract 10 g/L, peptone 10 g/L, glucose 20 g/L) and were collected upon reaching the exponential growth phase (10 $OD_{660}$). Prior to the acquisition of the parameters stated below, the cells were diluted in filtered water at a concentration of $10^6$ cells/mL: the samples thus diluted were analysed.

The parameters taken into consideration for the purpose were "Forward Scatter" (FSC) and "Side Scatter" (SSC). The FSC parameter allows the population to be characterized based on the dimension and the aggregation state of the individual cells, while the SSC parameter indicates its intracellular granularity/density: the latter parameter is influenced by the presence of granules at the cytoplasmic level and by the size of the cell membranes.

Figure 4:
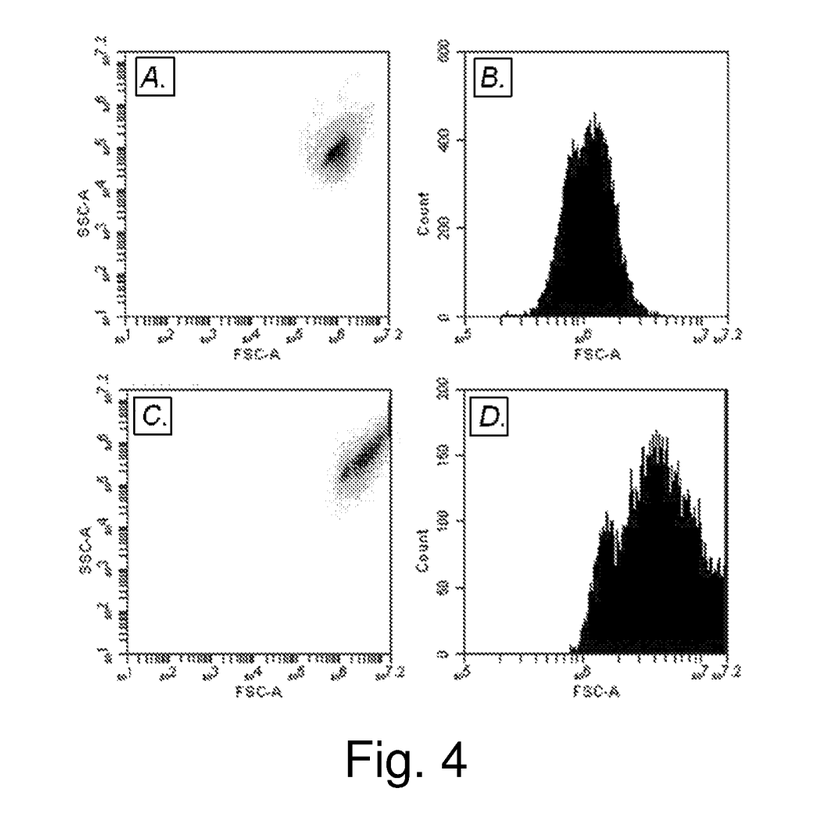
FIG. 4 A-D show results of Example 3 and the modification of the cell morphology of the variant of oleaginous yeast of the species *Trichosporon oleaginosus* DSM 32508: study through flow cytofluorimetry

By analysing the dispersion graphs, provided in FIG. 4, the differences in distribution of the population of the wild-type strain of oleaginous yeast of the species *Trichosporon oleaginosus* ATCC 20509 (A.) and in the variant of oleaginous yeast of the species *Trichosporon oleaginosus* DSM 32508 (C.) can be noted, both in terms of the FSC value and the SSC value. In detail, the histogram graphs highlight that the distribution of the population of the wild-type strain of oleaginous yeast of the species *Trichosporon oleaginosus* ATCC 20509 (B.) is more homogeneous in terms of size, while in the case of the variant of oleaginous yeast of the species *Trichosporon oleaginosus* DSM 32508 the distribution is more heterogeneous (D.). Comparing the graphs provided in B. and D. a "shift" can also be noted in the FSC value of the population towards the right, which indicates not only a larger cell size of the variant of oleaginous yeast of the species *Trichosporon oleaginosus* DSM 32508 with respect to the wild-type strain of oleaginous yeast of the species *Trichosporon oleaginosus* ATCC 20509, but also the presence of cell aggregates. The presence of these aggregates is also confirmed by the images collected under the microscope [FIG. 2(B.)].

The mean values of the parameters FSC and SSC are shown in Table 3 and indicated as arbitrary units (a.u.). Comparing the values of the FSC parameter, it can be deduced that the variant of oleaginous yeast of the species *Trichosporon oleaginosus* DSM 32508 has larger sizes compared to the wild-type strain of oleaginous yeast of the species *Trichosporon oleaginosus* ATCC 20509. An increase is also observed in the intracellular granularity/density indicated by the parameter SSC. In correspondence with the values FSC and SSC, the Coefficient of Variance (CV) is also provided (in brackets): this parameter indicates the dispersion of the values within the population, hence indicating the degree of uniformity thereof.

TABLE 3

|  | ATCC 20509 | DSM 32508 |
| --- | --- | --- |
| FSC (a.u.) | 1257 (49%) | 6380 (76%) |
| SSC (a.u.) | 105 (80%) | 876 (132%) |

In conclusion, the analyses performed through flow cytofluorimetry demonstrate that the morphology and the intracellular structure of the variant of oleaginous yeast of the species *Trichosporon oleaginosus* DSM 32508 are very different from those of the wild-type strain of oleaginous yeast of the species *Trichosporon oleaginosus* ATCC 20509 from which it derives.

EXAMPLE 4 (Genotypic Characterization of the Variant of Oleaginous Yeast of the Species *Trichosporon oleaginosus* DSM 32508)

In this example, the characterization process of the variant of oleaginous yeast of the species *Trichosporon oleaginosus* DSM 32508 is described, through genomic DNA sequencing and bioinformatic analysis of the mutations present compared with the genomic DNA sequence of the wild-type strain of oleaginous yeast of the species *Trichosporon oleaginosus* ATCC 20509 from which it derives.

For that purpose, the genomic DNA was extracted from cultures of both strains (the variant of oleaginous yeast of the species *Trichosporon oleaginosus* DSM 32508 and the wild-type strain of oleaginous yeast of the species *Trichosporon oleaginosus* ATCC 20509) realized in "YEPD" medium (Yeast extract 10 g/L, Peptone 10 g/L, glucose 20 g/L) for one night, and purified with the commercial kit DNeasy Blood & Tissue kit by Quiagen (cat. Num 69504) following the instructions provided by the manufacturer.

The platform used for sequencing is the Illumina HiSeq2500 system. The FASTQ sequences were generated with the Illumina Casava system, version 1.8.3. The sequencing quality was checked with Illumina Chastity and subsequently with FASTQC version 0.10.0. The sequencing quality was improved using "Trim sequences" version 8.5.1. The fragments thus generated were assembled in contiguous regions ("contig") using the "De novo assembly" option of the CLS Genomics Workbench program version 8.5.1 and reviewed with Pilon version 1.8, as stated by Walker B. J. et al, in "*Pilon: an integrated tool for comprehensive microbial variant detection and genome assembly improvement*", "PLoS One" (2014), Nov. 19, 9(11), e112963; DOI:10.1371/journal.pone.0112963.

The "contigs" were assembled in "supercontigs" using SSPACE Premium scaffolder version 2.3, as stated by Boetzer M. et al, in "*Scaffolding pre-assembled contigs using SSPACE*", "Bioinformatics" (2011), Feb. 15, 27(4): 578-9, doi:10.1093/bioinformatics/btq683, Epub 2010 Dec. 12.

The "gaps" were closed using GapFiller version 1.10, as stated by Boetzer M. et al, in "*Toward almost closed genomes with GapFiller*", "Genome Biology" (2012), Jun. 25, 13(6):R56, DOI:10.1186/gb-2012-13-6-r56.

The annotation of the genome was done with the Database Prokka Genome System (http://vicbioinformatics.com/) and with the database AUGUSTUS v3.0.1

Analysis of the sequences allowed the identification of 2177 contiguous regions ("contig") of dimensions that vary between 119195 and the 301 base pairs (bps), for a total of 19,601,063 base pairs (bps). This value is in line with the size of the genomic DNA of yeasts phylogenetically similar to the genus Trichosporon, therefore it is considered that the libraries obtained represent the complete genome of the variant of oleaginous yeast of the species Trichosporon oleaginosus DSM 32508, and the corresponding wild-type strain of oleaginous yeast of the species Trichosporon oleaginosus ATCC 20509 from which it derives. The sequences of the two genomic DNAs were compared to each other using the "Map Reads to Reference" and "Quality-based Variant Detection" software by CLCbio.

The mutations identified were confirmed by checking the existence in both sequencing directions and determining the accuracy therefore through the "phred" value.

In total, in the genomic DNA of the variant of oleaginous yeast of the species Trichosporon oleaginosus DSM 32508, 647 mutations were highlighted (comprising substitutions, deletions and insertions of nucleotides): 131 mutations lead to a change in the sequence of the corresponding protein and they are shown in Table 1 and Table 2.

EXAMPLE 5 (Sensitivity of the Variant of Oleaginous Yeast of the Species Trichosporon oleaginosus DSM 32508 to the Antibiotic Caspofungin)

In this example, the sensitivity of the variant of oleaginous yeast of the species Trichosporon oleaginosus DSM 32508 to the antibiotic caspofungin was evaluated. In fact, as described in Garcia L. et al, "BMC Genomics" (2015), DOI:10.1186/s12864-015-1879-4, mutants of defective fungi in the synthesis of chitin show greater sensitivity to the antibiotic caspofungin. In light of the results of the genomic analysis of the variant of oleaginous yeast of the species Trichosporon oleaginosus DSM 32508, which highlighted the presence of mutations affecting the genes coding a protein with chitin synthase activity, the sensitivity to this antibiotic was therefore evaluated.

For this purpose a sample of cells of a wild-type strain of oleaginous yeast of the species Trichosporon oleaginosus ATCC 20509 and a sample of cells of the variant of oleaginous yeast of the species Trichosporon oleaginosus DSM 32508 were inoculated, in two different flasks, in "YEPD" medium (yeast extract 10 g/L, peptone 10 g/L, glucose 20 g/L): the flasks were placed in an agitated incubator, at 30° C., for one night. Subsequently, the cells were collected through centrifugation at 1500 g for 5 minutes, washed in sterile water, then re-suspended in 1 ml of sterile water obtaining a suspension that was plated on Petri dishes containing a solid "YEPD" medium (agar 20 g/L, yeast extract 10 g/L, peptone 10 g/L, glucose 20 g/L) containing different concentrations of caspofungin: 30 ng/mL, 60 ng/mL, 90 ng/mL, 120 ng/mL. On said plates, spots of 10 µL of said suspension were plated, diluted in sterile water so as to contain about $10^5$, $10^4$, $10^3$, $10^2$ and 10 cells. The plates were incubated for 3 days at 30° C. to allow the growth of the cells.

Figure 5:
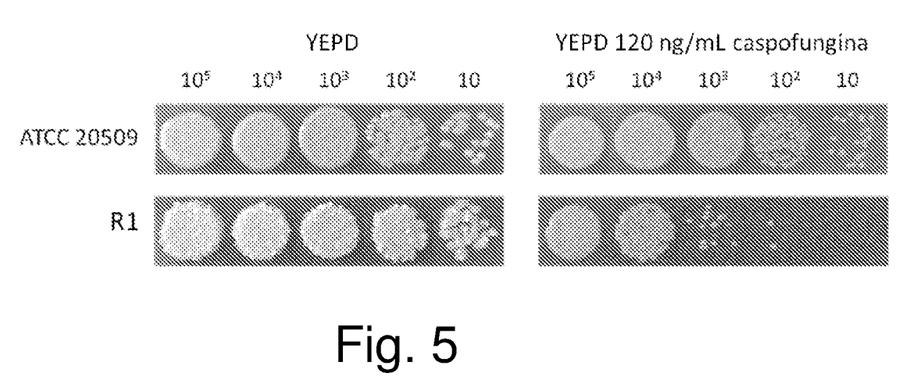
FIG. 5 shows results of Example 5 in assessing the sensitivity of the variant of oleaginous yeast of the species *Trichosporon oleaginosus* DSM 32508 to the antibiotic caspofungin.

The results of the different sensitivity were much more appreciable in the "YEPD" medium with 120 ng/mL of caspofungin (FIG. 5). The variant of oleaginous yeast of the species Trichosporon oleaginosus DSM 32508, like what happens with the strains of defective fungi in the synthesis of chitin, is more sensitive to the wild-type strain of oleaginous yeast of the species Trichosporon oleaginosus ATCC 20509, showing lower growth capacity in the presence of caspofungin, hence confirming its defect in the synthesis of chitin.

EXAMPLE 6 (Culture for the Production of Lipids in a Bioreactor)

In this example, the growth and accumulation of lipids of cells of the wild-type strain of oleaginous yeast of the species Trichosporon oleaginosus ATCC 20509 was evaluated and of cells of the variant of oleaginous yeast of the species Trichosporon oleaginosus DSM 32508.

For this purpose a sample of cells of a wild-type strain of oleaginous yeast of the species Trichosporon oleaginosus ATCC 20509 and a sample of cells of the variant of oleaginous yeast of the species Trichosporon oleaginosus DSM 32508 were inoculated, in two different 500 mL flasks, in 100 ml of "YEPD" medium (yeast extract 10 g/L, peptone 10 g/L, glucose 20 g/L): the flasks were placed in an agitated incubator, at 30° C., for one night.

The cell suspensions obtained were used to separately inoculate 20 litre bioreactors in which 6 L of liquid lipogenesis medium were arranged (glucose 100 g/L, corn steep liquor 50 g/L, yeast extract 2 g/L, potassium dihydrogen phosphate [$KH_2PO_4$] 6 g/L, magnesium sulfate heptahydrate [$MgSO_4.7H_2O$] 0.3 g/L, sodium chloride [NaCl] 0.06 g/L, calcium chloride dihydrate [$CaCl_2.2H_2O$] 0.06 g/L).

The volume of inoculum for each strain is that necessary for obtaining about 6 L of cell suspension having 0.5 $OD_{660}$.

The growth took place under aerobic conditions through the insufflation of air and variable agitation between 600 rpm and 900 rpm modulated with air flow so as to maintain the concentration of dissolved oxygen ($DO_2$) equal to 30% of the saturation value, and at a pH of about 5.0, maintained through the addition, when necessary, of some drops of a solution of KOH 5 M or of $H_2SO_4$ 10% (vol/vol).

The process was carried out in batch mode for the first 20 hours. Subsequently and up to 24 hours a nitrogen feed was provided, i.e. corn steep liquor (1.25 g/L) and ammonium sulfate (5.5 g/L). From 24 hours until the end of the process, a 600 g/L glucose solution was fed, so as to maintain constant the concentration of glucose at about 30 g/L throughout the whole process (90 hours in total).

After 90 hours of growth, a sample of culture broth was taken from both bioreactors and the following values were determined, operating as described above:

wild-type strain of oleaginous yeast of the species Trichosporon oleaginosus ATCC 20509 had reached a cell concentration of 89 g/L (i.e. quantity of biomass expressed as dry weight in cells in g per litre of culture), containing 47% by weight of lipids (i.e. a quantity of accumulated lipids expressed as a percentage ratio between weight of lipids and total dry weight), equal to a total of 42 g/L (i.e. quantity of accumulated lipids expressed as a concentration of lipids in g/L); the maximum productivity was 0.52 g/L/h of lipids, with a total yield of 0.17 g of lipids per g of glucose consumed; variant of oleaginous yeast of the species Trichosporon oleaginosus DSM 32508 had reached a cell concentration of 111 g/L (i.e. quantity of biomass expressed as dry weight in cells in g per litre of culture), containing 60% by weight of lipids (i.e. a quantity of accumulated lipids expressed as a percentage ratio between weight of lipids and total dry weight), equal to a total of 67 g/L (i.e. quantity of accumulated lipids expressed as a concentration of lipids in g/L); the maximum productivity was 0.77 g/L/h of lipids, with a total yield of 0.20 g of lipids per g of glucose consumed.

EXAMPLE 7 (Measurement of Viscosity and Centrifugability of the Culture Broth)

On the cultures obtained as described above in Example 6, the viscosity and density were measured (through a Stabinger SVR 3000 Anton Paar microviscometer, shear rate 1/1000, at 30° C.) and the centrifugability (through spin test using a Thermo Scientific IEC CL31R Multispeed centrifuge with fixed angle rotor AC 100.10A) at different inoculation times.

In particular, the spin tests were carried out by centrifuging aliquots of the culture broth, equal to 10 mL, at 5000 rpm, for 10 minutes and measuring the concentration factor with respect to the culture broth as such.

The results obtained are reported in Table 4 and in Table 5.

TABLE 4

Wild-type strain of the oleaginous yeast of the species *Trichosporon oleaginosus* ATCC 20509

| Time (h) | Dry weight (g/L) | Lipids (%) | Viscosity (cP) | Density (g/cm$^3$) | Concentration |
|---|---|---|---|---|---|
| 40 | 62 | 25 | 50 | 1.044 | 2× |
| 65 | 83 | 41 | 86 | 1.041 | 1.25× |
| 90 | 89 | 47 | 119 | 1.040 | 1.2× |

TABLE 5

Variant of oleaginous yeast of the species *Trichosporon oleaginosus* DSM 32508

| Time (h) | Dry weight (g/L) | Lipids (%) | Viscosity (cP) | Density (g/cm$^3$) | Concentration |
|---|---|---|---|---|---|
| 40 | 71 | 19 | 17 | 1.041 | 2× |
| 65 | 99 | 48 | 30 | 1.040 | 2× |
| 90 | 111 | 60 | 47 | 1.028 | 2× |

From the data reported in Tables 4 and 5 it can be deduced that the culture broth obtained from the variant of oleaginous yeast of the species *Trichosporon oleaginosus* DSM 32508 has lower viscosity and greater centrifugability than that one obtained from the wild-type strain of oleaginous yeast of the species *Trichosporon oleaginosus* ATCC 20509.

The invention claimed is:

1. A variant of oleaginous yeast of the species *Trichosporon oleaginosus* deposited on May 17, 2017 at the Leibniz-Institut DSMZ—Deutsche Sammlung von Mikroorganismen und Zellkulturen GmbH—InhoffenstraBe 7 B 38124 Braunschweig (Germany) with the deposit number DSM 32508.

2. A process for the production of lipids comprising:
   inoculating a culture medium with the oleaginous yeast variant of claim 1 in a culture device and culturing to obtain a culture broth;
   separating said culture broth to obtain a suspension of a concentrated oleaginous cellular biomass and an aqueous phase; and
   extracting the intracellular lipids accumulated inside the yeast cells in the suspension.

3. The process for the production of lipids according to claim 2, wherein said process culture broth is maintained:
   at a temperature of 10° C. to 40° C.; and/or
   for a time of 40 hours to 200 hours; and/or
   under aerobic conditions; and/or
   at a pH between 4.5 to 7.0.

4. The process for the production of lipids according to claim 2, wherein said oleaginous yeast variant is inoculated in the culture medium at a 1% to 5% v/v of the total volume of culture medium, is obtained from a previous culture of said variant of oleaginous yeast of the species *Trichosporon oleaginosus* DSM 32508, and is cultured for 6 to 24 hours after inoculation.

5. The process for the production of lipids according to claim 2, wherein the culture medium comprises glucose as a carbon source and ammonium sulfate [(NH$_4$)$_2$SO$_4$] as a nitrogen source.

6. The process for the production of lipids according to claim 2, wherein said culture broth is cultured using a fed-batch culture technique.

7. The process for the production of lipids according to claim 2, wherein 15 hours to 25 hours after the inoculation, said culture broth is cultured using a fed-batch culture technique, adding at least one further nitrogen source to add a total amount of nitrogen ranging from 0.5 g/L to 5 g/L.

8. The process for the production of lipids according to claim 2, wherein 15 hours to 25 hours after the inoculation, said culture broth is cultured using a fed-batch culture technique, adding an aqueous solution of glucose so as to maintain a constant concentration of glucose of 25 g/L to 50 g/L.

* * * * *